(12) United States Patent
Lagos González

(10) Patent No.: US 8,957,207 B2
(45) Date of Patent: Feb. 17, 2015

(54) METHODS FOR PRODUCING PHYCOTOXINS

(75) Inventor: Marcelo Santiago Lagos González, Santiago (CL)

(73) Assignee: Proteus S.A., Santiago (CL)

( * ) Notice: Subject to any disclaimer, the term of this patent is extended or adjusted under 35 U.S.C. 154(b) by 0 days.

(21) Appl. No.: 13/243,119

(22) Filed: Sep. 23, 2011

(65) Prior Publication Data
US 2012/0053344 A1 Mar. 1, 2012

Related U.S. Application Data

(63) Continuation-in-part of application No. PCT/IB2010/051188, filed on Mar. 18, 2010, and a continuation-in-part of application No. PCT/IB2010/051187, filed on Mar. 18, 2010.

(51) Int. Cl.
*C07D 487/14* (2006.01)
*C12P 17/18* (2006.01)
*C12N 1/12* (2006.01)

(52) U.S. Cl.
CPC ............... *C12N 1/12* (2013.01); *C07D 487/14* (2013.01); *C12P 17/182* (2013.01)
USPC .......................................... 544/251; 435/119

(58) Field of Classification Search
CPC .. C07D 475/14; C07D 487/14; C07D 487/04; C07D 471/14; A61K 31/525
See application file for complete search history.

(56) References Cited

U.S. PATENT DOCUMENTS 3,004,894 A 10/1961 Johnson
3,328,259 A 6/1967 Anderson
(Continued)

FOREIGN PATENT DOCUMENTS

BE 776769 12/1971
EP 0043738 9/1982
(Continued)

OTHER PUBLICATIONS

Hu, "Interactions of Neosaxitoxin with the Sodium Channel of the Frog Skeletal Muscle Fiber", The Journal of General Physiology, 1991, 97, pp. 561-578.*
(Continued)

*Primary Examiner* — San-Ming Hui
*Assistant Examiner* — Andrew Lee
(74) *Attorney, Agent, or Firm* — Pabst Patent Group LLP

(57) ABSTRACT

Methods for producing phycotoxins from natural sources, wherein the phycotoxins have a definite compositional profile are described herein. In one embodiment, the phycotoxins are produced by cyanobacteria. In one embodiment, the phycotoxins are produced by continuously culturing cyanobacteria under strictly controlled conditions in order to produce a definite compositional profile. In another embodiment, organic nutrients are added to the culture that allows for higher concentrations of neosaxitoxin and saxitoxin or gonyaulatoxins 2 and 3 per weight of the algae. The phycotoxins are isolated primarily from the bacteria but can also be isolated from the culture medium. In one embodiment, the cyanobacteria produce only neosaxitoxin and saxitoxin in a ratio of about 6:1, 5:1, 4:1, or 3:1. In a preferred embodiment, the amount of saxitoxin is less than 20% by weight of the total amount of neosaxitoxin and saxitoxin produced. In another embodiment, the cyanobacteria produce only GTX2 and GTX 3.

8 Claims, 1 Drawing Sheet

(56) References Cited

U.S. PATENT DOCUMENTS

| | | | |
|---|---|---|---|
| 3,374,144 | A | 3/1968 | Emmanuel |
| 3,957,996 | A | 5/1976 | Adams |
| 3,966,934 | A | 6/1976 | Adams |
| 4,001,413 | A | 1/1977 | Adams |
| 4,022,899 | A | 5/1977 | Adams |
| 4,029,793 | A | 6/1977 | Adams |
| 4,029,794 | A | 6/1977 | Adams |
| 4,313,958 | A | 2/1982 | LaHann |
| 4,401,663 | A | 8/1983 | Buckwalter |
| 4,443,473 | A | 4/1984 | Buckwalter |
| 4,460,602 | A | 7/1984 | Buckwalter |
| 4,493,848 | A | 1/1985 | LaHann |
| 4,537,776 | A | 8/1985 | Cooper |
| 4,544,668 | A | 10/1985 | Janusz |
| 4,544,669 | A | 10/1985 | LaHann |
| 4,564,633 | A | 1/1986 | LaHann |
| 4,654,323 | A | 3/1987 | Beitner |
| 4,820,720 | A | 4/1989 | Sanders |
| 4,863,970 | A | 9/1989 | Patel |
| 4,973,468 | A | 11/1990 | Chiang |
| 4,997,853 | A | 3/1991 | Bernstein |
| 5,006,342 | A | 4/1991 | Cleary |
| 5,008,289 | A | 4/1991 | Bernstein |
| 5,013,759 | A | 5/1991 | Berman |
| 5,045,565 | A | 9/1991 | Gardner |
| 5,099,030 | A | 3/1992 | Gardner |
| 5,134,166 | A | 7/1992 | Bernstein |
| 5,618,563 | A | 4/1997 | Berde |
| 5,700,485 | A | 12/1997 | Berde |
| 5,716,637 | A | 2/1998 | Anselem |
| 5,858,397 | A | 1/1999 | Lim |
| 6,030,974 | A | 2/2000 | Schwartz |
| 6,326,020 | B1 | 12/2001 | Kohane |
| 6,407,088 | B1 | 6/2002 | Dong |
| 6,455,066 | B1 | 9/2002 | Fischer |
| 6,673,363 | B2 | 1/2004 | Luo |
| 2002/0161013 | A1 | 10/2002 | Liu |
| 2002/0197284 | A1 | 12/2002 | Luo |
| 2004/0172354 | A1 | 9/2004 | Charnley |
| 2005/0202093 | A1 | 9/2005 | Kohane |
| 2005/0214325 | A1 | 9/2005 | David |
| 2006/0271466 | A1 | 11/2006 | Gorbatovsky |
| 2008/0045553 | A1 | 2/2008 | Wilson |
| 2008/0154792 | A1 | 6/2008 | Maggioncalda |

FOREIGN PATENT DOCUMENTS

| | | |
|---|---|---|
| EP | 750909 | 1/1997 |
| GB | 1370904 | 10/1974 |
| GB | 2153223 | 8/1985 |
| WO | 8505621 | 12/1985 |
| WO | 9311798 | 6/1993 |
| WO | 9401166 | 1/1994 |
| WO | 9405265 | 3/1994 |
| WO | 9641616 | 12/1996 |
| WO | 9851290 | 11/1998 |
| WO | 0141550 | 6/2001 |
| WO | 0222129 | 3/2002 |
| WO | 0241915 | 5/2002 |
| WO | 2006034624 | 4/2006 |
| WO | 2006091719 | 8/2006 |
| WO | 2008063603 | 5/2008 |
| WO | 2009143174 | 11/2009 |
| WO | 2009143175 | 11/2009 |
| WO | 2010041255 | 4/2010 |
| WO | 2010109386 | 9/2010 |
| WO | 2010109387 | 9/2010 |
| WO | 2010117996 | 10/2010 |
| WO | 2010129864 | 11/2010 |

OTHER PUBLICATIONS

Lagos, "The first evidence of paralytic shellfish toxins in the freshwater cyanobacterium *Cylindrospermopsis raciborskii*", isolated from Brazil, Toxicon, 1999, 37, pp. 1359-1373.*

Llewellyn, "Saxitoxin, a toxic marine natural product that targets a multitude of receptors", Natural Product Reports, 2006, 23, pp. 200-222.*

Nixdorf, "Phytoplankton assemblages and steady state in deep and shallow eutrophic lakes—an approach to differentiate the habitat properties of Oscillatoriales", Hydrobiologia, 2003, 502, pp. 111-121.*

Shimizu, "Biosynthesis of Red Tide Toxins", Marine Toxins, 1990, 418, pp. 21-28.*

Flores, Production of Ammonium Dependent on Basic L-Amino Acids by Anacystis nidulans, Archives of Microbiology, 1982, 131, pp. 91-94.*

Mazur-Marzec, Characterization of phycotoxins produced by cyanobacteria, International Journal of Oceanography and Hydrobiology, 2006, XXXV (1), pp. 85-109.*

Bolch and Blackburn, "Isolation and purification of Australian isolates of the toxic cyanobacterium*Microcystis aeruginosa* Kütz", J. Appl. Phycology, 8, 5-13 (1996).

Castro, et al., "The effect of temperature on growth and production of paralytic shellfish poisoning toxins by the cyanobacterium *Cylindrospermopsis raciborskii* C10", Toxicon, 44:483-89 (2004).

Guevremont, et al., "Comparison of cation-exchange and chelating cation-exchange resins for the concentration of saxitoxin", Analy. Chimica Acta., 255:163-68 (1991).

Llewellyn, "Saxitoxin, a toxic marine natural product that targets a multitude of receptors", Nat. Prod. Rep., 23:200-222 (2006).

Long, et al., "Cellular microcystin content in N-Limited *Microcystis aerginosa* can be predicted from growth rate", Appl. Enviro. Microbiol., 67(1):278-83 (2001).

Media recipes used in CMAR ,CMAR Methods. Retrieved Aug. 2, 2008  http://www.marine.csiro.au/microalgae/methods/Media%20CMARC%20recipes.htm.

Pomati, et al., "The purine degradation pathway: possible role in paralytic shellfish toxin metabolism in the cyanobacterium *Planktothrix* sp. FP1", Environ. Int., 27:463-470 (2001).

Pomati, et al., "Evidence for differences in the metabolism of saxitoxin and C1+2 toxins in the freshwater cyanobacterium *Cylindrospermopsis raciborskii* T3", Biochem.Biophys. Acta., 1674:60-67 (2004).

Rositano, et al., Ozonation of nom and algal toxins in four treated waters, Wat. Rev 35(1):23-32 (2001).

Soto, et al., "The effects of chloramphenicol, arginine and temperature on PST-production by *Cylindrospermopsis raciborskii* strain D9", Proceedings of the 12th Intl. Conf. on Harmful Algae, Copenhagen (2008).

Sayfritz, et al., "Determination of paralytic shellfish poisoning toxins in Norwegian shellfish by liquid chromatography with fluorescence and tandem mass spectrometry detection", Toxicom, 52:330-40 (2008).

International Search Reoport PVT/IB2010/051188.

Aboul-Fadl, "Antisense oligonucleotides: the state of the art", Curr Med Chem 12:2193-214 (2005).

Akerman, et al., "Penetration enhancers and othe factors governing percutaneous local anaesthesia with lidocaine", Acta Pharma. Et toxicological, 45(1):58-65 (1979).

Adjei and Garren, "Pulmonary delivery of peptide drugs: effect of particle size on bioavailability of leuprolide acetate in healthy male volunteers", J Pharm. Res, 7:565-9 (1990).

Alam, et al., "Design of liposome to improve encapsulation efficiency of gelonin and its effect on immunoreactivity and ribosome inactivating property", Mol Cell Biochem 112:97-107 (1992).

Barnes, "Sativex: clinical efficacy and tolerability in the treatment of symptoms of multiple sclerosis and neuropathic pain", Expert Opin Pharmacother 7:607-15 (2006).

Barnet, et al., "Tissue injury from tricyclic antidepressants used as local anesthetics" Anesth Analg, 101(6):1838-1843 (2005).

Barnet, et al., "Site 1 sodium channel blockers prolong the duration of sciatic nerve blockade from tricyclic antidepressants", Pain 110:432-8 (2004).

Bartlett, "Phosphorus assay in column chromatography", J. Biol. Chem., 234(3):466-468 (1959).

(56) References Cited

OTHER PUBLICATIONS

Bates, et al., "A chemical assay for saxitoxin. Improvements and modifications", J. of agricultural and food chem., 26(1):252-254 (1978).
Befort, et al., "Selective up-regulation of the growth arrest DNA damage-inducible gene Gadd45 alpha in sensory and motor neurons after peripheral nerve injury", Eur J Neurosci., 18(4):911-922 (2003).
Benoit, et al., "Pharmacologic correlation between local anesthetic-induced myotoxicity and disturbances of intracellular calcium distribution", Toxicol. Appl. Pharmacol., 52:187-198 (1980).
Berde, et al., "Tetrodotoxin-bupivacaine-epinephrine combinations for prolonged local anesthesia", Marine Drugs, 9:2717-28 (2011).
Bernards and Hill, "Physical and chemical properties of drug molecules governing their diffusion through the spinal meninges", Anesthesiology, 77(4):750-6 (1992).
Binshtok, et al., "Inhibition of nociceptors by TRPV1-mediated entry of impermeant sodium channel blockers", Nature, 449:607-610 (2007).
Cereda, et al., "Liposomal formulations of prilocaine, lidocaine and mepivacaine prolong analgesic duration", Can J Anaesth., 53(11):1092-1097 (2006).
Chaim-Matyas, et al., "Encapsulation of the cobra cytotoxin P4 in liposomes", Biotechnol Appl Biochem, 17(Pt 1):31-6 (1993).
Choi and Maibach, "Liposomes and niosomes as topical drug delivery systems", J, Pharmacal and Biophys. Res., 18(5):209-19 (2005).
Clarkson, et al., "Mechanism for bupivacaine depression of cardiac conduction: fast block of sodium channels during the action potential with slow recovery from block during diastole", Anesthesiology, 62:396-405 (1985).
Cortesi, et al., "Sugar cross-linked gelatin for controlled release: microspheres and disks", Biomaterials 19:1641-9 (1998).
de Araujo, et al., "Encapsulation of mepivacaine prolongs the analgesia provided by sciatic nerve blockade in mice", Can J Anaesth., 51(6):566-572 (2004).
de Paiva and Dolly, "Light chain of botulinum neurotoxin is active in mammalian motor nerve terminals when delivered via liposomes", FEBS Lett 277:171-4 (1990).
Drager, et al., Prolonged intercostal nerve blockade in sheep using controlled-release of bupivacaine and dexamethasone from polymer microspheres Anesthesiology, 89(4):969-979 (1998).
Epstein-Barash, et al., "Prolonged duration local anesthesia with minimal toxicity", PNAS, 106(17):7125-30 (2009).
Estebe, et al., "Amitriptyline neurotoxicity: dose-related pathology after topical application to rat sciatic nerve", Anesthesiology, 100:1519-25 (2004).
Fang, et al., "Synergistically enhanced transdermal prrmration and tropical analgesia of tetracaine gel containing menthol and ethanol in experimental and clinical studies", Eu J Pharm and Biopharm., 68:735-40 (2008).
Fisher, et al., "Detection of intravascular injection of regional anaesthetics in children", Can. J. Anaesth., 44: 592-8 (1997).
Fozzard, et al., "Mechanism of local anesthetic drug action on voltage-gated sodium channels", Curr. Pharm, Des., 11:2671-2686 (2005).
Fraser, et al., "Intravesical liposome administration—a novel treatment for hyperactive bladder in the rat", Urology, 61: 656-663 (2003).
Freitas and Frezard, "Encapsulation of native crotoxin in liposomes: a safe approach for the production of antivenom and vaccination against *Crotalus durissus terrificus*venom", Toxicon 35:91-100 (1997).
Garcia, et al., "Route of metabolization and detoxicarion of paralytric shellfish toxins in humans", Toxicon, 55:135-44 (2010).
Gerner, et al., "Amitriptyline versus bupivacaine in rat sciatic nerve blockade", Anesthesiology, 94(4):661-667 (2001).
Grant, et al., "A novel liposomal bupivacaine formulation to produce ultralong-acting analgesia", Anesthesiology, 101(1):133-137 (2004).

Grant, et al., "Analgesic duration and kinetics of liposomal bupivacaine after subcutaneous injection in mice", Clin Exp Pharmacol Physiol., 30(12):966-968 (2003).
Grant, et al., "DRV liposomal bupivacaine: preparation, characterization, and in vivo evaluation in mice", Pharm Res., 18(3):336-343 (2001).
Gregoradis, et al., "Engineering liposomes for drug delivery: progress and problems", Trends Biotechnol 13, 527-37 (1995).
Gregoriadis and Allison, "Entrapment of proteins in liposomes prevents allergic reactions in pre-immunised mice", FEBS Lett 45:71-4 (1974).
Gregoriadis and Ryman, "Liposomes as carriers of enzymes or drugs: a new approach to the treatment of storage diseases", Biochrem. J., 124:58P (1971).
Gregoriadis, et al., "Improving the therapeutic efficacy of peptides and proteins: a role for polysialic acids", Intl. J. Pharm., 300:125-30 (2005).
Gregoriadis, "The carrier potential of liposomes in biology and medicine (second of two parts)", N Engl J Med 295:765-70 (1976).
Haller, et al., "Differential neurotoxicity of tricyclic antidepressants and novel derivatives in vitro in a dorsal root ganglion cell culture model", Eur J Anaesthesiol., 24(8):702-708 (2007).
Harden, "Chronic neuropathic pain. Mechanisms, diagnosis and treatment", The Neurologist, 11(2):111-22 (2005).
Hoebeeck, et al., "Rapid detection of VHL exon deletions using real-time quantitative PCR", Lab. Invest., 85(1):24-33(2005).
Jia, et al., "Prolongation of sciatic nerve blockade by in situ cross-linked hyaluronic acid", Biomaterials, 25(19):4797-4804 (2004).
Kao, "Tetrodotoxin, saxitoxin and their significance in the study of excitation phenomena," Pharmacological Rev., 18(2):999-1049 (1966).
Kohane, et al., "A re-examination of tetrodotoxin for prolonged duration local anesthesia", Anesthesiology, 89:119-31 (1998a).
Kohane, et al., "Biocompatibility of lipid-protein-sugar particles containing bupivacaine in the epineurium", J Biomed Mater Res., 59(3):450-459 (2002).
Kohane, et al., "Effects of adrenergic agonists and antagonists on tetrodotoxin-induced nerve block", Reg Anesth Pain Med, 26;239-45 (2001).
Kohane, et al., "Prolonged duration local anesthesia from tetrodotoxin-enhanced local anesthetic microspheres", Pain, 104(1-2):415-21 (2003).
Kohane, et al., "Sciatic nerve blockade in infant, adolescent, and adult rats: a comparison of ropivacaine with bupivacaine", Anesthesiology, 89:1199-1208 (1998b).
Kohane, et al., "The local anesthetic properties and toxicity of saxitonin homologues for rat sciatic nerve block in vivo", Reg Anesth Pain Med., 25:52-9 (2000).
Kohane, et al., "Vanilloid receptor agonists potentiate the in vivo local anesthetic activity of percutaneously injected site 1 sodium channel blockers", Anesthesiology, 90:524-34(1999).
Kushla, et al., "Noninvasive assessment of anesthetic activity of topical lidocaine formulations", J Pharm Sci, 82:1118-22 (1993).
Kuznicki, et al., "Structure of neosaxitoxin", Am Chem Soc., 0002-7863/7:6791-3 (1978).
Lim, et al. "The Quaternary Lidocaine Derivtive, QX-314, Produces Long-lasting Local Anesthesia in Animal Models In Vivo", Anesthesiology, 107:305-11 (2007).
Lirk, et al., "The neurotoxic effects of amitriptyline are mediated by apoptosis and are effectively blocked by inhibition of caspase activity", Anesth Analg., 102(6):1728-33 (2006).
Luo, et al., "Injury type-specific calcium channel alpha 2 delta-1 subunit up-regulation in rat neuropathic pain models correlates with antiallodynic effects of gabapentin", J Pharmacol Exp Ther., 303(3):1199-1205 (2002).
Malinovsky, et al,, "A dose-response study of epidural liposomal bupivacaine in rabbits", J Control Release., 60(1):111-119 (1999).
Mandel and Lee, "Listeriolysin O-liposome-mediated cytosolic delivery of macromolecule antigen in vivo: enhancement of antigen-specific cytotoxic T lymphocyte frequency, activity, and tumor protection", Biochim Biophys Acta 1563:7-17 (2002).

(56) References Cited

OTHER PUBLICATIONS

Masters, et al., "Prolonged regional nerve blockade by controlled release of local anesthetic from a biodegradable polymer matrix" Anesthesiology, 79(2):340-346 (1993).
McLure and Rubin, "Review of local anaesthetic agents", Minerva Anesthesiol., 71:59-74 (2005).
Mearow, et al., "Stress-mediated signaling in PC12 cells—the role of the small heat shock protein, Hsp27, and Akt in protecting cells from heat stress and nerve growth factor withdrawal", Journal of neurochemistry, 83(2):452-462 (2002).
Middleton, "Mechanism of action of surfactants on water binding properties of isolated stratum corneum", J Soc Cosmet Chem.,20:399-403 (1969).
Minko, et al., "New generation of liposomal drugs for cancer", Anticancer Agents Med Chem 6, 537-52 (2006).
Myers, et al., "Neurotoxicity of local anesthetics: altered perineurial permeability, edema, and nerve fiber injury", Anesthesiology, 64:29-35 (1986).
Nakagomi, et al., "Expression of the activating transcription factor 3 prevents c-Jun N-terminal kinase-induced neuronal death by promoting heat shock protein 27 expression and Akt activation", J Neurosci., 23(12):5187-5196 (2003).
Newton, et al., "Dorsal root ganglion neurons show increased expression of the calcium channel alpha2delta-1 subunit following partial sciatic nerve injury", Brain Res Mol Brain Res., 95(1-2):1-8 (2001).
Olivera, et al., "Diversity of Conus Neuropeptides," Science, 249:257-63, (1990).
Oshima, "Postcolumn derivatization liquid chromatographic method for paralytic shellfish toxins", J of AOAC Intl., 78(2):528-32 (1995).
Padera, et al., "Tetrodotoxin for prolonged local anesthesia with minimal myotoxicity", Muscle Nerve, 34:747-53 (2006).
Padera, et al., "Local myotoxicity from sustained release of bupivacaine from microparticles", Anesthesiology, 108(5):921-928 (2008).
Pere, et al., "Local myotoxicity of bupivacaine in rabbits after continuous supraclavicular brachial plexus block", Reg Anesth, 18(5):304-307 (1993).
Ribaud, et al., "Organization of stratum corneum lipids in relation to permeability: influence of sodium lauryl sulfate and preheating", Pharm Res 11:1414-8 (1994).
Rodriguez-Navarro, et al., "Neosaxition as a local anesthetic", Anesthesiology, 106:339-45 (2007).
Rodriguez-Navarro, et al., "Potenriation of local anethetic activity of neosaxitoxin with bupivacaine or epinephrine developmenr of a long-acting pain blocker", Neurotox. Res., 16:408-15 (2009).
Rodriguez-Navarro, et al., "Comparison of neosaxitoxin versus bupivacaine via port infiltration for postoperarive analgesia following laparoscopic cholecystectomy", Reg. Anesth. Pain Med., 38:103-9 (2011).
Ruetsch., et al., "From cocaine to ropivacaine: the history of local anesthetic drugs", Curr. Top. Med. Chem., 1:175-182 (2001).
Sagie and Kohane, "Prolonged sensory-selective neve blockade", Natl. Acad. Sci, 107(8):3740-5 (2010).
Sakura, et al., "Local anesthetic neurotoxicity does not result from blockade of voltage-gated sodium channels", Anesth Analg., 81:338-46 (1995).
Sapra, et al., "Ligand-targeted liposomes for cancer treatment", Curr. Drug Deliv., 2:369-81 (2005).
Schneider, et al., "A preferential inhibition of impulses in C-fibers of the rabbit vagus nerve by veratridine, an activator of sodium channels," Anesthesiology,74:270-81 (1991).
Scholz, "Mechanisms of (local) anaesthetics on voltage-gated sodium and other ion channels", Br J. Anaesth., 89:52-61 (2002).
Scurlock, et al. "Tetraethylammonium derivatives: Ulatralong-acting Local Anesthetics", Anesthesiology, 54:265-9 (1981).
Shankarappa, et al., "Lipsome-encapsulated saxitoxin in the trearment of nerve injury-induced chronic neuropathic pain", 41st annual meeting Society-for-neuroscience, Nov. 12-16, Washington DC (2011).
Shankarappa, et al., "Prolonged nerve blockage delays the onset of neuropathic pain", PNAS, 109(43):17555-60 (2012b).
Shankarappa, et al., "Duration and local toxicity of sciatic nerve blockade with coinjected site 1 sodium-channel blockers and quaternary lidocaine derivatives", Reg. Anesthesia Pain Med., 37(5):483-9 (2012a).
Simons, et al., "Effect of chemical permeation enhancers on nerve blockade", Mol Pharmaceutics, 6:265-73 (2009).
Sleno, et al., "Gas-phase dissociation reactions of protonated saxitoxin and neosaxition", J am Soc Mass Spectrom, 15:462-77 (2004).
Soares, et al., "Neuronal and glial expression of the adhesion molecule TAG-1 is regulated after peripheral nerve lesion or central neurodegeneration of adult nervous system", Eur J Neurosci., 21(5):1169-1180 (2005).
Song, et al., "Axotomy-induced dopaminergic neurodegeneration is accompanied with c-Jun phosphorylation and activation transcription factor 3 expression", Exp Neurol., 209(1):268-278 (2008).
Strichartz, "Structural determinanrs of affinity of saxitoxin for neuronal sodium channels", J Gen. Physiol., 84:281-305 (1984).
Szoka, et al., "Comparative properties and methods of preparation of lipid vesicles (liposomes)", Annual review of biophysics and bioengineering, 9:467-508 (1980).
Thalhammer, et al., "Neurologic evaluation of the rat during sciatic nerve block with lidocaine," Anesthesiology, 82(4)1013-25 (1995).
Tyagi, et al., "Urodynamic and immunohistochemical evaluation of intravesical capsaicin delivery using thermosensitive hydrogel and liposomes", J Urol 171:483-9 (2004).
Vandesompele, et al., "Accurate normalization of real-time quantitative RT-PCR data by geometric averaging of multiple internal control genes", Genome biology, 3(7):RESEARCH0034 (2002).
Wagner, et al., "Salitoxin and Procaine Act Independently on Separate Sites of the Sodium Channel," Pflugers Arch., 364:65-70 (1976).
Wall, et al., "Autonomy following peripheral nerve lesions: experimental anesthesia dolorosa", Pain., 7(2):103-111 (1979).
Wylie, et al., "Respiratory and neuromuscular effects of neosaxition in anesthetized sheep", Abstract for presentation at the ASA annual meeting, 3 pages, Oct. 2011.
Wylie, et al., "Respirarory, neuromuscular, and cardiovascular effects of neosaxitoxin in isoflurane-anesthetized sheep", Reg. Anes. Pain Med., 00:1-7 (2012).
Wu, et al., Lipid-based nanoparticulate drug dellvry systems. In D Thassu (Ed.), Nanoparticulate Drug Delivery Systems, pp. 89-98 (2007).
Yahalom, et al., "Spinal anesthesia in infant rats: development of a model and assessment of neurologic outcomes", Anesthesiology, 114(6):1325-35 (2011).
Yamashita, et al., "A comparison of the neurotoxic effects on the spinal cord of tetracaine, lidocaine, bupivacaine, and ropivacaine administered intrathecally in rabbits", Anesth Analg, 97(2):512-519 (2003).
Zanen, et al., "The optimal particle size for parasympathicolytic aerosols in mild asthmatics", Int J Pharm., 114:111-5. (1995).
Zimmer, et al., "Cardiotoxic and neurotoxic effects after accidental intravascular bupivacaine administration. Therapy with lidocaine propofol and lipid emulsion", Anaesthesist, 56(5):449-453 (2007).
Zimmermann, "Ethical guidelines for investigations of experimental pain in conscious animals", Pain, 16(2)109-110 (1983).

* cited by examiner

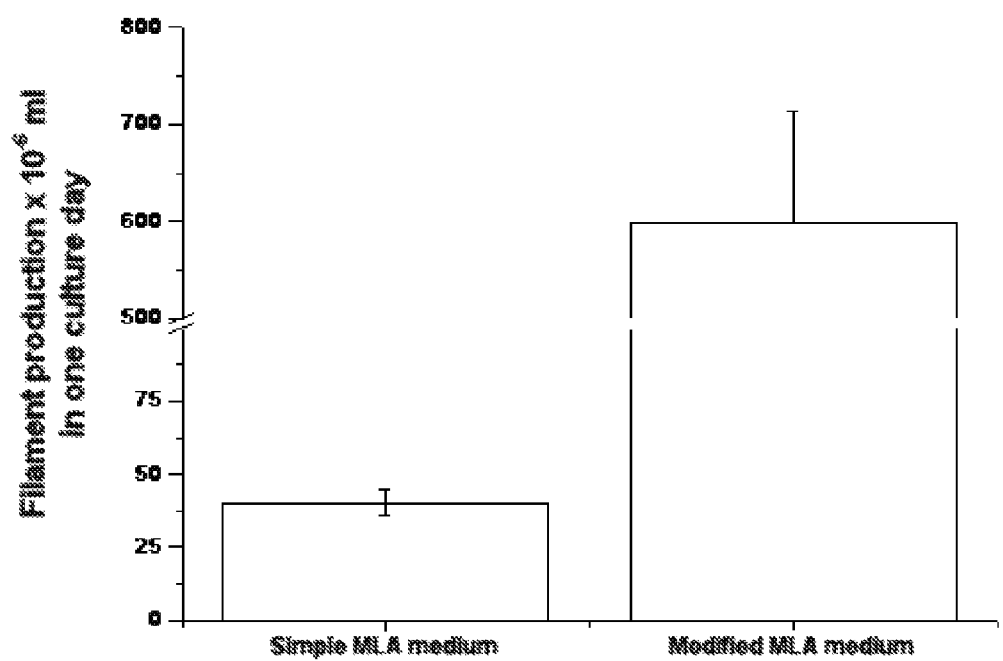

METHODS FOR PRODUCING PHYCOTOXINS

FIELD OF THE INVENTION

This invention is in the field of methods of production of phycotoxins from natural sources, particularly methods for the continuous production of phycotoxins from cyanobacteria.

CROSS REFERENCE TO RELATED APPLICATIONS

This application claims priority under 35 U.S.C. 371 to PCT/IB2010/051188 filed Mar. 18, 2010, PCT/IB2010/051187 filed Mar. 18, 2010, Chilean Patent Application No. 722-2009 filed Mar. 24, 2009, and Chilean Patent Application No. 723-2009 filed Mar. 24, 2009, all of which are incorporated by reference.

BACKGROUND OF THE INVENTION

Phycotoxins ([phyco=seaweeds and algae] plus toxins) are a diverse group of substances produced by various aquatic plants in marine and fresh waters throughout the world. Not all aquatic plants produce toxins; and among those that do, not all, even from the same genera and species, produce toxins at all times and under all circumstances. Such toxins are associated with large fish kills and major kills of marine mammals. These toxins can also be found in shellfish.

Phycotoxins can also be produced by cyanobacteria. Five cyanobacteria are known to produce shellfish paralyzing phycotoxins, each of them having a characteristic composition with respect to the amount and type of phycotoxins produced (e.g., profile of phycotoxins):

(1) *Cylindrospermopsis raciborskii*, isolated from Brazil;
(2) *Aphanizomenon flos-aquae*, isolated from Portugal;
(3) *Anabaena raciborskii* , isolated from Australia;
(4) *Lyngbya wollei*, isolated from North America; and
(5) *Aphanizomenon* (Aph) *gracile* (Lemm) Lemm (Pereira P LMECYA40).

Neosaxitoxin and saxitoxin are two specific phycotoxins produced by dinoflagellate species of the genera *Alexandrium* sp., *Piridinium* sp. and *Gimnodinium* sp. and cyanobacteria.

Neosaxitoxin and saxitoxin acts as specific blockers of the voltage-dependent sodium channels present in excitable cells. Due to the inhibition of sodium channels, the transmission of a nervous impulse is blocked preventing the release of neurotransmitters at the neuromotor junction, which prevents muscular contraction. Due to these physiological effects, these compounds are potentially useful in pharmacology when used as muscular activity inhibitors in pathologies associated with muscular hyperactivity, such as muscular spasms and focal dystonias, when administered locally. These compounds can also inhibit sensory pathways and generate an anesthetic effect when administered locally.

However, these compounds are not available commercially in the quantities necessary to manufacture pharmaceutical compositions. Therefore, there exists a need for improved methods to produce phycotoxins having a definite compositional profile, particularly phycotoxin mixtures containing only neosaxitoxin and saxitoxin or GTX 2 and GTX 3.

Therefore, it is an object of the invention to provide improved methods for producing phycotoxins having a definite compositional profile, particularly phycotoxin mixtures containing only neosaxitoxin and saxitoxin or GTX 2 and GTX 3.

It is another object of the invention to provide a continuous method for culturing cyanobacteria for the production of phycotoxins having a definite compositional profile, particularly phycotoxin mixtures containing only neosaxitoxin and saxitoxin or GTX 2 and GTX 3.

It is another object of the invention to produce substantially pure phycotoxins using the methods described herein.

SUMMARY OF THE INVENTION

Large scale methods for producing phycotoxins from natural sources, wherein the phycotoxins have a definite compositional profile, have been developed. The phycotoxins are produced by culturing cyanobacteria under strictly controlled conditions in order to produce a definite compositional profile. In a more particular embodiment, organic nutrients are added to the culture that allows for higher concentrations of neosaxitoxin and saxitoxin or gonyaulatoxins 2 and 3 per weight of the cyanobacteria. The phycotoxins are isolated primarily from the bacteria (e.g., cell pellet fraction) but can also be isolated from the culture medium.

In one embodiment, the cyanobacteria produce only neosaxitoxin and saxitoxin in a ratio of about 6:1, 5:1, 4:1, or 3:1. In a preferred embodiment, the amount of saxitoxin is less than 20% by weight of the total amount of neosaxitoxin and saxitoxin produced. In another embodiment, the cyanobacteria produce only GTX2 and GTX 3.

BRIEF DESCRIPTION OF THE DRAWINGS

FIG. 1 is a bar graph showing the production of filaments in one culture day using MLA Medium modified with methionine, arginine and allantoic acid in continuous light conditions and the unmodified medium with light:darkness cycling.

DETAILED DESCRIPTION OF THE INVENTION

I. Definitions

"Definite compositional profile", as used herein, refers to a mixture of particular phycotoxins. For example, a definite compositional profile can refer to a mixture containing only one, two, or three phycotoxins. In one embodiment, the mixture contains only two phycotoxins. In one embodiment, the mixture contains only neosaxitoxin (NEO) and saxitoxin (STX), wherein NEO is the major component (e.g., 60-80%). In another embodiment, the mixture contains only GTX2 and GTX3, wherein GTX 2 is the major component.

"Organic nutrients", as used herein, refers to one or more organic compounds that, when added to the culture medium, promote formation of one or more particular phycotoxins. In one embodiment, the organic nutrients promote the formation of neosaxitoxin and saxitoxin or GTX2 and GTX3.

II. Methods for the Continuous Production of Phycotoxins

Methods for producing phycotoxins from a natural source, wherein the mixture of phycotoxins has a definite compositional profile are described herein.

A. Cyanobacteria

In one embodiment, the phycotoxins are produced from cyanobacteria, also referred to as blue-green algae. In theory any cyanobacteria can be used provides it produces, or can be induced t produce, a mixture of phycotoxins having a definite compositional profile. Suitable cyanobacteria include, but are not limited to, *Cylindrospermopsis raciborskii, Aphanizomenon flos-aquae, Aphanizomenon* (Aph) *issatschenkoi* (Usacev) *Proskina-Lavrenco, Anabaena circinalis, Lyngbya wollei, Aphanizomenon gracile* (Lemm) Lemm, and *Aphanizomenon elenkinii* var. *Gracile Kashtanova*.

In a preferred particular embodiment, the cyanobacterium is *Aphanizomenon gracile* (Lemm) Lemm and/or *Aphanizomenon elenkinii* var. *Gracile Kashtanova*. *Aphanizomenon gracile* (Lemm) Lemm can be collected from a variety of sources. However, in one embodiment, *Aphanizomenon gracile* (Lemm) Lemm was collected from Crato Lake, a reservoir in Portugal, isolated, and codified as LMECYA 41. A culture of a single cyanobacterium isolated from the sample was grown at 25° C. for 2-4 weeks until reaching a suitable development state for subsequent production.

B. Culture Medium

The cyanobacteria can be cultured in any medium that is suitable for the particular cyanobacteria to be cultured. In one embodiment, the cyanobacteria are cultured in a modified MLA medium. MLA medium is derived from ASM-1 medium. The composition of MLA medium and the method of making thereof is described in Kütz, *J. Appl. Phycology*, 8, 5-13 (1996). The medium contains the following ingredients: $MgSO_4 \cdot 7H_2O$, $NaNO_3$, $K_2HPO_3$, $H_3BO_3$, $H_2SeO_3$, biotin, vitamin $B_{12}$, thiamine HCl, $Na_2EDTA$, $FeCl_3 \cdot 6H_2O$, $NaHCO_3$, $MnCl_2 \cdot 4H_2O$, $CuSO_4 \cdot 5H_2O$, $ZnSO_4 \cdot 7H_2O$, $CoCl_2 \cdot 6H_2O$, $Na_2MoO_4 \cdot 2H_2O$, and $CaCl_2 \cdot 2H_2O$. Other ingredients that can be added to the medium include HCl (0.1 N), NaOH (0.1 N), KBr, $Na_2CO_3$, $K_2HPO_4$, $(NH_4)_6Mo_7O_{24} \cdot 4H_2O$, $Cd(NO_3)_2 \cdot 4H_2O$, $Ca(NO_3)_2 \cdot 4H_2O$, $Co(NO_3)_2 \cdot 6H_2O$, $Cr(NO_3)_3 \cdot 9H_2O$, $V_2O_5$, $MnSO_4 \cdot H_2O$, $NiSO_4(NH_4)_2SO_4 \cdot 6H_2O$, $Al_2(SO_4)_3K_2SO_4 \cdot 24H_2O$, Na $Na_2WO_4 \cdot 2H_2O$, KY, and combinations thereof.

Concentrations ranges for these materials are shown in the table below:

| Compound | Minimal concentration (g/l) | Maximal concentration (g/l) |
| --- | --- | --- |
| $MgSO_4 \times 7H_2O$ | 3.71E−02 | 6.18E−02 |
| $NaNO_3$ | 1.28E−01 | 2.13E−01 |
| $K_2HPO_4$ | 2.61E−02 | 4.35E−02 |
| $H_3BO_3$ | 1.85E−03 | 3.09E−03 |
| $H_2SeO_4$ | 9.68E−04 | 1.61E−03 |
| Biotin | 3.75E−08 | 6.25E−08 |
| Vitamin $B_{12}$ | 3.75E−08 | 6.25E−08 |
| Thiamine HCl | 7.50E−05 | 1.25E−04 |
| $CuSO_4 \times 5H_2O$ | 7.50E−06 | 1.25E−05 |
| $ZnSO_4 \times 7H_2O$ | 1.65E−05 | 2.75E−05 |
| $CoCl_2 \times 6H_2O$ | 7.50E−06 | 1.25E−05 |
| $NaMoO_4 \times 2H_2O$ | 4.50E−06 | 7.50E−06 |
| $Na_2EDTA$ | 3.27E−03 | 5.45E−03 |
| $FeCl_3 \times 6H_2O$ | 1.19E−03 | 1.98E−03 |
| $NaHCO_3$ | 4.50E−04 | 7.50E−04 |
| $MnCl_2 \times H_2O$ | 2.70E−04 | 4.50E−04 |

1. Organic Nutrients

In one embodiment, one or more organic nutrients which promote production of one or more particular phycotoxins are added to the culture medium. In one embodiment, one or more organic nutrients are added to the culture medium to promote production of only neosaxitoxin and saxitoxin or only GTX 2 and GTX3.

In one embodiment, the organic nutrients are selected from arginine, methionine, allantoic acid, and combinations thereof. In a particular embodiment, the organic nutrients arginine, methionine, and allantoic acid are added to the culture medium. The organic nutrients are present in an effective amount to promote production of a mixture of phycotoxins having a definite compositional profile. In one embodiment, the concentration of arginine is from about 2 to about 3.5 mM, the concentration of methionine is about 1 to about 2.2 mM, and the concentration of allantoic acid is from about 0.7 to about 1.3 mM in the final composition of the culture medium. In a particular embodiment, the concentration of arginine, methionine, and allantoic acid is about 2.8 mM, 1.7 mM, and 1 mM, respectively. The use of organic nutrients, particularly arginine, to drive the production of particular compounds contrasts with the prior art. For example, it has been reported that the use of organic nutrients has little or no effect on phycotoxin production in dinoflagellates. Further, it has been reported that incorporation of arginine into a culture medium containing *Cylindrospermopsis raciborskii*, which produced primarily saxitoxin and GTX 2/3 and small amount of dcSTX and dcGTX2/3, caused a 48% decrease in saxitoxin production for the D9 strain of the bacteria.

Cyanobacteria produced using the culture medium described above are resistant to contamination since the culture medium contains little, if any, materials needed to for the growth of other microorganisms. The MLA medium is a natural selection medium which is specific for the culturing of cyanobacteria.

C. Culture Conditions

Once the culture medium has been prepared, the cyanobacteria are typically inoculated at a concentration of 20-40 million filaments per 3 L of culture medium. The cyanobacteria can be cultured in any suitable container, such as a 250 ml Erlenmeyer flask. The container is placed in a culture chamber maintained at a temperature of about 15° C. to about 30° C., preferably from about 20° C. to about 25° C., more preferably at about 22° C.±2° C. The inoculum is generated using a light:darkness cycles of 16:8 hours.

The resulting inoculum is transferred into reactors, which are maintained under sterile conditions. The cyanobacteria are cultured at a temperature of about 15° C. to about 30° C., preferably from about 20° C. to about 25° C., more preferably at about 22° C.±2° C. The reactors can be sealed reactors or open reactors.

Cyanobacteria can be characterized by their division cycle. Depending on the division cycle, it is possible to remove 20-40% of the total reactor volume to isolate phycotoxins, provided an equivalent amount of fresh, sterile medium is used to replace the withdrawn portion. *Aphanizomenon gracile* (Lemm) Lemm has a reported division cycle of 0.33/day. This means that after 3 days, the cell mass of the culture has doubled. In one embodiment, one liter of medium from each 3-L reactor is withdrawn every 1-2 days for isolation of the phycotoxins. The volume removed is replaced with one liter of fresh, sterilized medium. Filament counting can be used to determine when a portion of the medium should be removed for isolation of the phycotoxins. The continuous withdrawal and replacement of medium every 1-2 provides a system for the continuous production of the cyanobacteria which produced phycotoxins. In a preferred embodiment, the time period between harvesting is less than 4 days.

Once the portion of the medium is removed, the medium is centrifuged to produce a cell pellet containing the filament-forming cyanobacteria. The presence of filaments is indicative of a healthy culture medium and can be used to assay growth and/or presence of contaminants in the medium. Filaments can be quantified using an inverted microscope. In addition to isolating phycotoxins from the cell pellet, phycotoxins may be isolated form the supernatant (i.e., the medium remaining after centrifugation). However, under optimal conditions, the amount of toxins isolated from the supernatant is typically less than 5% of the total content obtained from the cell pellet.

Lighting conditions can also be used to increase phytotoxin production. For example, as described above, during the growth and development stage, the cyanobacteria were subject to light and darkness cycles, such as 16 hours of illumination and 8 hours of darkness. However, once the inoculum has been obtained and cultured to produce phycotoxins, the light and darkness cycles can be manipulated to maintain the cyanobacteria in the exponential growth phase. For example, the cyanobacteria can be subject to constant illumination with no darkness period. Illumination is preferably direct illumination. This is possible because cyanobacteria are photosynthetic organisms which require light and reach optimal development during the exponential growth phase. Alternative, the cyanobacteria can be exposed to different light and darkness cycles. Illumination can be done using natural light and/or artificial light, such as fluorescent tubes and/or white light emitting diodes (LEDs). Manipulation of the light and dark cycles in combination with the continuous withdrawal of medium allows one to maintain the cyanobacteria in the exponential growth phase, which maximizes phytotoxin production. Production of bacteria as described herein results in 60-125 times higher productivities.

Generally, incubation times of about 10 days were used to obtain optimal growth of the bacteria and a suitable number of filaments for processing. During the incubation time, temperature and/or lighting conditions were monitored. pH, salinity, ventilation, and agitation were not specifically monitored. However, these parameters can be varied as necessary to maintain optimal growth of the bacteria. The approximate amount of neosaxitoxin produced was $1.72 \times 10^{-15}$ moles (femtomoles) of toxin per filament or $5.418 \times 10^{-13}$ grams of toxin per filament.

III. Phycotoxins

The methods described herein can be used to produce mixtures of phycotoxins having a definite compositional profile. In one embodiment, the mixture contains no more than two phycotoxins. In one embodiment, the phycotoxins have the general formula shown below including the stereochemistry shown:

Specific phycotoxins are described in the table below:

| Molecular Weight | R1 | R2 | R3 | R4 | Toxin |
|---|---|---|---|---|---|
| 242.3 | H | H | H | H | doSTX |
| 258.3 | H | H | H | H | dcSTX |
| 274.3 | OH | H | H | H | dcNEO |
| 301.3 | H | H | H | $CONH_2$ | STX |
| 317.3 | OH | H | H | $CONH_2$ | NEO |
| 337.3 | H | $OSO_3^-$ | H | H | doGTX2 |
| 337.3 | H | H | $OSO_3^-$ | H | doGTX3 |
| 353.3 | H | $OSO_3^-$ | H | H | dcGTX2 |
| 353.3 | H | H | $OSO_3^-$ | H | dcGTX3 |
| 369.3 | OH | $OSO_3^-$ | H | H | dcGTX1 |
| 369.3 | OH | H | $OSO_3^-$ | H | dcGTX4 |
| 380.4 | H | H | H | $CONHSO_3^-$ | B1 |
| 396.4 | OH | H | H | $CONHSO_3^-$ | B2 |
| 396.4 | H | $OSO_3^-$ | H | $CONH_2$ | GTX2 |
| 396.4 | H | H | $OSO_3^-$ | $CONH_2$ | GTX3 |
| 412.4 | OH | $OSO_3^-$ | H | $CONH_2$ | GTX1 |
| 412.4 | OH | H | $OSO_3^-$ | $CONH_2$ | GTX4 |
| 475.4 | H | $OSO_3^-$ | H | $CONHSO_3^-$ | C1 |
| 475.4 | H | H | $OSO_3^-$ | $CONHSO_3^-$ | C2 |
| 491.4 | OH | $OSO_3^-$ | H | $CONHSO_3^-$ | C3 |
| 491.4 | OH | H | $OSO_3^-$ | $CONHSO_3^-$ | C4 |

Other phycotoxins are described in Llewellyn, *Nat. Prod. Rep.*, 23, 200-222 (2006).

In one embodiment, the methods described herein produce a mixture of phycotoxins containing only neosaxitoxin and saxitoxin, wherein the ratio of neosaxitoxin to saxitoxin is about 6:1, preferably about 5:1, more preferably about 4:1, most preferably about 3:1. In a particular embodiment, the mixture of phycotoxins contains only neosaxitoxin and saxitoxin, wherein the concentration of saxitoxin is less than 20% by weight of the total weight of the two compounds.

In another embodiment, the methods described herein produce a mixture of phycotoxins containing only gonyaulatoxins, such as a mixture GTX2 and GTX3. The ratio of GTX2 to GTX3 is about 9:1, preferably about 8:2, more preferably from about 7:3, most preferably from about 6:4.

The use of the modified MLA medium described herein resulted in a significant increase in the amount of specific phycotoxins produced compared to the used unmodified MLA medium. In one embodiment, the amount of neosaxitoxin produce using modified MLA medium is at least 10, 15, 20, 25, 30, 35, or more times greater than the amount produced using unmodified MLA medium.

EXAMPLES

Example 1

Preparation of Culture Media

To prepare the culture medium, concentrated stock solutions of micronutrients, mineral salts and vitamins were prepared. All solutions were prepared with distilled water.

The Vitamin Stock Solution (Solution A) was prepared according to the amounts provided in Table 1:

TABLE 1

| Composition of the Vitamin stock Solution (Solution A) | | | |
|---|---|---|---|
| | Concentration (mg/ml) | Volume (ml) | Final concentration (mg/ml) |
| Biotin | 0.1 | 0.05 | 0.00005 |
| Vitamin B12 | 0.1 | 0.05 | 0.00005 |
| Thiamine HCl | | | 0.1 |

1 mg of biotin was dissolved in 10 ml of distilled water. Similarly, 1 mg of vitamin B12 was dissolved in 10 ml of distilled water. 0.05 ml of each of these two solutions was mixed with 10 mg of thiamine HCl and distilled water to a final volume of 100 ml.

The Micronutrient Stock Solution (Solution B) was prepared from primary solutions of CuSO4.5H2O (1 g/l), ZnSO4.7H2O (2.2 g/l), CoCl2.6H2O (1 g/l), NaMoO4.2H2O (0.6 g/l).

10 ml of each primary solution was added to 800 ml of the solution described in Table 2.

TABLE 2

Micronutrient Stock Solution

| | Concentration (g/l) | Amount (g) in 800 ml |
|---|---|---|
| $Na_2EDTA$ | 5.45 | 4.36 |
| $FeCl_3 \cdot 6H_2O$ | 1.975 | 1.58 |
| $NaHCO_3$ | 0.75 | 0.6 |
| $MnCl_2 \cdot H_2O$ | 0.45 | 0.36 |

The solution was diluted to a final volume of 1 L with distilled water.

250 ml of a concentrated 40× stock of MLA medium was prepared by adding the volumes indicated for each component in Table 3 to 130 ml of distilled water.

TABLE 3

MLA medium composition

| Component | Solution (g/l) | Volume (ml) |
|---|---|---|
| $MgSO_4 \cdot 7H_2O$ | 49.4 | 10 |
| $NaNO_3$ | 85 | 20 |
| $K_2HPO_4$ | 6.96 | 50 |
| $H_3BO_3$ | 2.47 | 10 |
| $H_2SeO_4$ | 1.29 | 10 |
| Vitamin Stock (solution A) | | 10 |
| Micronutrient Stock (solution B) | | 10 |

For media to be sterilized by filtration through a 0.22 micron membrane, 1 L of MLA culture medium was prepared by combining the following volumes in Table 4.

TABLE 4

Culture medium to be sterilized by filtration

| | (g/l) | Volume (ml) |
|---|---|---|
| Distilled water | | 964 |
| 40× MLA Stock | | 25 |
| $NaHCO_3$ | 16.9 | 10 |
| $CaCl_2 \cdot 2H_2O$ | 29.4 | 1 |

For media to be sterilized using an autoclave (e.g., 121° C. for 15 minutes), the media are prepared by combining the volumes shown in Table 5 and adjusting the pH to 7.5-8 with a suitable acid, such as hydrochloric acid (e.g., HCl).

TABLE 5

Culture medium to be sterilized by autoclave

| | (g/l) | Volume (ml) |
|---|---|---|
| Distilled water | | 973 |
| 40× MLA Stock | | 25 |
| $NaHCO_3$ | 16.9 | 1 |
| $CaCl_2 \cdot 2H_2O$ | 29.4 | 1 |

The final concentrations of the various components are shown in Table 6.

TABLE 6

Culture medium

| Compound | Concentration in the ready-to-use medium (g/l) |
|---|---|
| $MgSO_4 \cdot 7H_2O$ | 4.94E-02 |
| $NaNO_3$ | 1.70E-01 |
| $K_2HPO_4$ | 3.48E-02 |
| $H_3BO_3$ | 2.47E-03 |
| $H_2SeO_4$ | 1.29E-03 |
| Biotin | 5.00E-08 |
| Vitamin B12 | 5.00E-08 |
| Thiamine HCl | 1.00E-04 |
| $CuSO_4 \cdot 5H_2O$ | 1.00E-05 |
| $ZnSO_4 \cdot 7H_2O$ | 2.20E-05 |
| $CoCl_2 \cdot 6H_2O$ | 1.00E-05 |
| $NaMoO_4 \cdot 2H_2O$ | 6.00E-06 |
| $Na_2EDTA$ | 4.36E-03 |
| $FeCl_3 \cdot 6H_2O$ | 1.58E-03 |
| $NaHCO_3$ | 6.00E-04 |
| $MnCl_2 \cdot H_2O$ | 3.60E-04 |

$NaHCO_3$ and $CaCl_2 \cdot 2H_2O$ are added as needed, since their concentration depends on the type of sterilization (filtration or autoclaving) used for the medium.

All the solutions can be stored refrigerated for up to 1 month.

Prior to culturing the bacteria, arginine, methionine and allantoic acid were added at final concentrations of 2.8 mM arginine, 1.7 mM methionine and 1 mM allantoic acid.

Example 2

Culture of *Aphanizomenon* (Aph) *gracile* (Lemm) Lemm

Each reactor containing 3 liters of the culture medium described in Example 1 was inoculated with 35 million filaments of *Aphanizomenon* (Aph) *gracile* (Lemm) *Lemm*. The reactors were maintained at a temperature of 22° C.±2° C., with permanent illumination from fluorescent tubes. Once the culture reached the exponential phase, one-third of the total reactor volume was collected (1 liter) and replaced with 1 liter of fresh medium. The culture had a doubling time of 0.33 times per day.

The removed culture medium containing cyanobacteria was centrifuged at 10,000 g for 20 minutes.

The yields obtained are expressed as a function of the number of filaments, since the presence of filaments (association of individual cells) is an indicator of the quality of the culture and of the permanent reproduction and development of the cells. A filament-rich culture is a "healthy" culture and is in permanent development. The cell pellet is a pellet formed of the filaments. The number of filaments for various batches is shown in Table 7.

TABLE 7

Number of Aphanizomenon (Aph) gracile (Lemm) filaments per milliliter of culture as a function of time

| Batch | Culture day | Filaments of cyanobacteria in the pellet per ml | Collected volume (ml) |
|---|---|---|---|
| 1 | Day 1 | 590,000 | 1000 |
| 2 | Day 2 | 598,000 | 1000 |
| 3 | Day 3 | 630,000 | 1000 |

TABLE 7-continued

Number of Aphanizomenon (Aph) gracile (Lemm) filaments per milliliter of culture as a function of time

| Batch | Culture day | Filaments of cyanobacteria in the pellet per ml | Collected volume (ml) |
|---|---|---|---|
| 4 | Day 4 | 596,000 | 1000 |
| 5 | Day 5 | 626,000 | 1000 |
| 6 | Day 6 | 788,000 | 1000 |
| 7 | Day 7 | 534,000 | 1000 |
| 8 | Day 8 | 756,000 | 1000 |
| 9 | Day 9 | 754,000 | 1000 |
| 10 | Day 10 | 614,000 | 1000 |
| 11 | Day 11 | 622,000 | 1000 |
| 12 | Day 12 | 608,000 | 1000 |
| 13 | Day 13 | 770,800 | 1000 |

The cell pellet of each batch is the volume obtained from one liter of culture harvested each day from the reactor. This can also be carried out every other day, to achieve a larger number of filaments. Under the culture conditions used, it is preferable to carry out the harvest no more than 4 days apart, to avoid culture deterioration and phytotoxin production decrease.

Example 3

Comparison of the Culture with Simple (Unmodified) MLA Medium and the Modified MLA Medium of the Present Invention FIG. 1 shows the difference between a culture of *Aphanizomenon gracile* in the simple (unmodified) MLA medium and a culture of *Aphanizomenon gracile* with the modified MLA culture medium containing the additives to promote production of neosaxitoxin and saxitoxin. The addition of arginine, methionine, and allantoic acid resulted in a significant increase in filament production which results in an increase in phycotoxin production.

Table 8 shows the concentration of the different phycotoxins in the supernatant and the yield of cyanobacterial filaments. Table 8 also indicates the concentration of filaments per ml of culture medium.

TABLE 8

Concentration of the different phycotoxins in the supernatant and the yield of cyanobacterial filaments

| Concentration in the supernatant | | | | Concentration of phycotoxin per filament | | Cyano. fil./ml* |
|---|---|---|---|---|---|---|
| neoSTX mM | STX mM | neoSTX µg/ml | STX µg/ml | neoSTX pg/fil. | STX pg/fil | |
| 8.98 | 3.5 | 2.83 | 1.05 | 2.42 | 0.9 | 1,170,000,00 |
| 13.66 | 4.91 | 4.3 | 1.47 | 3.44 | 1.18 | 1,250,000,00 |
| 3.42 | 1.03 | 1.08 | 0.31 | 1.71 | 0.49 | 630,000,00 |
| 17.82 | 4.78 | 5.61 | 1.43 | 9.42 | 2.41 | 596,000,00 |
| 17.81 | 4.02 | 5.61 | 1.21 | 13.17 | 2.83 | 426,000,00 |
| 7.66 | 1.47 | 2.41 | 0.44 | 4.94 | 0.91 | 488,000,00 |
| 10.87 | 2.19 | 3.42 | 0.66 | 10.25 | 1.97 | 334,000,00 |
| 10.52 | 2.07 | 3.31 | 0.62 | 4.38 | 0.82 | 756,000,00 |
| 10.77 | 1.96 | 3.39 | 0.59 | 7.47 | 1.3 | 454,000,00 |
| 17.24 | 2.99 | 5.43 | 0.9 | 13.12 | 2.16 | 414,000,00 |
| 5.31 | 0.41 | 1.67 | 0.12 | 5.19 | 0.38 | 322,000,00 |
| 12.26 | 2.17 | 3.86 | 0.65 | 9.47 | 1.59 | 408,000,00 |
| 9.84 | 1.94 | 3.1 | 0.58 | 17.42 | 3.27 | 178,000,00 |

STX: saxitoxin
neoSTX: neosaxitoxin
Cyano. fil.: cyanobacterial filaments
*Cyanobacterial filaments are associations of 20 to 100 cyanobacterial cells. These cyanobacteria form filaments in solution and those filaments are counted using the magnification of an inverted microscope.

Table 9 shows different phycotoxin production batches. It is shown that the mean yield of phycotoxin per filament is much higher when using the modified MLA medium with the growth conditions described herein in comparison with the culture in simple (unmodified) MLA medium as described in the prior art. For example, the amount of neosaxitoxin produced using the modified MLA medium is more than 25 times the amount produced using non-modified MLA medium.

TABLE 9

Production of neosaxitoxin and saxitoxin as a function of the number of filaments in the modified MLA medium and unmodified MLA medium

| | Production of phycotoxins in modified MLA medium and permanent illumination | | Production of phycotoxins in simple MLA medium with light:darkness cycling | |
|---|---|---|---|---|
| | neoSTX pg/fil. | STX pg/fil | neoSTX pg/fil. | STX pg/fil |
| | 2.42 | 0.9 | 0.09 | 0.03 |
| | 3.44 | 1.18 | 0.13 | 0.04 |
| | 1.71 | 0.49 | 0.06 | 0.02 |
| | 9.42 | 2.41 | 0.35 | 0.09 |
| | 13.17 | 2.83 | 0.49 | 0.1 |
| | 4.94 | 0.91 | 0.18 | 0.03 |
| | 10.25 | 1.97 | 0.38 | 0.07 |
| | 4.38 | 0.82 | 0.16 | 0.03 |
| | 7.47 | 1.3 | 0.28 | 0.05 |
| | 13.12 | 2.16 | 0.48 | 0.08 |
| | 5.19 | 0.38 | 0.19 | 0.01 |
| | 9.47 | 1.59 | 0.35 | 0.06 |
| | 17.42 | 3.27 | 0.65 | 0.12 |
| Average | 7.88 | 1.55 | 0.29 | 0.06 |

The yields obtained in these experiments show a surprising and unexpected increase in the production of phycotoxins (e.g., neosaxitoxin and saxitoxin) per cyanobacterial filament cultured in the modified MLA medium (Table 8), when compared to the production of the cyanobacterial filaments cultured with unmodified MLA in small culture flasks, with no continuous aeration, and with light (day): darkness (night) cycles (Table 9).

In the examples described herein, cyanobacteria are always in the logarithmic growth phase, with permanent illumination 24 hours a day and with permanent collection of cyanobacteria, inducing permanent growth by adding new nutrients in a volume that is equivalent to the volume collected in each harvest.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method for the continuous production of phycotoxins from cyanobacteria, the method comprising (a) inoculating a culture medium with the cyanobacteria, wherein the cyanobacteria is selected from the group consisting of *Cylindrospermopsis raciborskii; Aphanizomenon flos-aquae; Aphanizomenon* (APh) *issatschenkoi* (usaceb) *Proskina-Lavrenco; Aphanizomenon gracile* (Lemm) Lemm; *Aphanizomenon elenkinii var. Gracile Kashtanova; Anabaena circinalis; Lyngbya wollei;* and combinations thereof, wherein the culture medium comprises $MgSO_4.7H_2O$, $NaNO_3$, $K_2HPO_4$, $H_3BO_3$, $H_2SeO_4$, biotin, vitamin B12, thiamine HCl, $CuSO_4.5H_2O$, $ZnSO_4.7H_2O$, $CoCl_2.6H_20$, $NaMoO_4.2H_2O$, $Na_2EDTA$, $FeCl_3.6H_2O$, $NaHCO_3$, and $MnCl_2.H_2O$, about 2 to about 3.5 mM arginine, about 1 to about 2.2 mM methionine, and about 0.7 to about 1.3 mM allantoic acid;

(b) culturing the cyanobacteria in the culture medium at a temperature from 15 to 30° C. under permanent natural or artificial illumination;

(c) collecting a volume of culture medium ranging from 20 to 40% of the total volume every 1 to 3 days and replacing the removed volume with fresh culture medium; and (d) harvesting the cyanobacteria to isolate the phycotoxins.

2. The method of claim 1, wherein the cyanobacteria is *Aphanizomenon gracile* (Lemm) Lemm.

3. The method of claim 1, wherein the cyanobacteria are cultured in a continuous light cycle.

4. The method of claim 1, wherein the cyanobacteria are cultured at a temperature from about 15° C. to about 25° C.

5. The method of claim 1, wherein the cyanobacteria are cultured at a temperature of about 22±2° C.

6. The method of claim 1, wherein the culture medium has a final arginine concentration of about 2.8 mM.

7. The method of claim 1, wherein the culture medium has a final methionine concentration of about 1.7 mM.

8. The method of claim 1, wherein the culture medium has a final allantoic acid concentration of about 1.0 mM.

* * * * *